United States Patent [19]

Deguchi et al.

[11] Patent Number: 4,847,395
[45] Date of Patent: Jul. 11, 1989

[54] GLYCIDYL COMPOUNDS

[75] Inventors: Yoshikuni Deguchi; Hiroshi Iwakiri; Kazunari Iwamoto; Kazuya Yonezawa, all of Hyogo, Japan

[73] Assignee: Kanegafuchi Kagaku Kogyo Kabushiki Kaisha, Osaka, Japan

[21] Appl. No.: 105,782

[22] Filed: Oct. 8, 1987

[30] Foreign Application Priority Data

Oct. 13, 1986 [JP] Japan ................. 61-242763

[51] Int. Cl.$^4$ ................. C07D 303/08
[52] U.S. Cl. ................. 549/552
[58] Field of Search ................. 549/552

[56] References Cited

U.S. PATENT DOCUMENTS 3,945,973  3/1976  Smith et al. ................. 549/552

FOREIGN PATENT DOCUMENTS 0125826  2/1979  European Pat. Off. .
0000763  11/1984  European Pat. Off. .

Primary Examiner—Glennon H. Hollrah
Assistant Examiner—Mark W. Russell
Attorney, Agent, or Firm—Armstrong, Nikaido, Marmelstein, Kubovcik & Murray

[57] ABSTRACT

Novel glycidyl compounds represented by general formula (I):

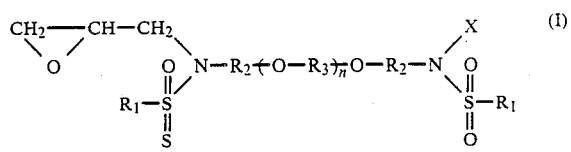

(wherein all the symbols are as defined in the appended claims), and a process for preparation of the glycidyl compounds are disclosed. The glycidyl compounds are prepared by reacting ethersulfonamide represented by general formula (III):

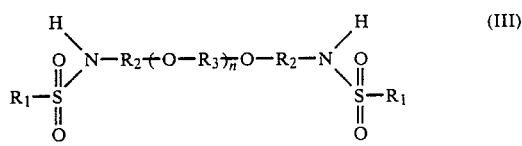

(wherein all the symbols are as defined in the appended claims) and epihalohydrin, and then reacting the resultant adduct with an aqueous caustic alkali solution.

13 Claims, 1 Drawing Sheet

GLYCIDYL COMPOUNDS

BACKGROUND OF THE INVENTION

1. Field of the Invention

The present invention relates to novel glycidyl compounds and a process for preparation thereof. More particularly it is concerned with novel glycidyl compounds which are liquid, are of good storage stability and can provide cured products excellent in flexibility and elongation and a process for preparation thereof.

2. Prior Art

Epoxy resins are used in various applications, for example, as paints, electric materials, adhesives, building materials, or matrix resins for fiber reinforced plastics (FRP). Their cured resins, however, are generally poor in flexibility and toughness, and cannot be said to sufficiently satisfy desired mechanical properties. Therefore, various flexibility imparting agents are used in combination to improve mechanical properties, such as impact resistance, heat impact resistance and adhesive properties of cured products. In this case, however, it is known that a reduction in properties such as tensile strength, modulus of elasticity and heat distortion temperature is accompanied.

In order to impart flexibility to cured products, a method of using glycidylamine containing polyalkylene ether in the main chain (Japanese Patent Application (OPI) No. 36209/79 (the term "OPI" as used herein means a "published unexamined patent application")) and a method of using polyalkylene ether amine as a curing agent (H. Kakiuchi, ed., *New Epoxy Resins*, Shokodo, Tokyo) are known. In the former method, the yield is as low as 60–70% and the glycidyl compounds are poor in storage stability. The latter method has a disadvantage in that the pot life of varnish is short.

SUMMARY OF THE INVENTION

As a result of investigations to develop a method whereby flexibility can be imparted without greatly reducing the mechanical strength of the cured product, there have been discovered glycidyl compounds which have a polyether main chain, can provide cured products having excellent flexibility, and are of good storage stability.

The present invention relates to novel glycidyl compounds containing at least one ether bond in the main chain thereof, as represented by the following general formula (I):

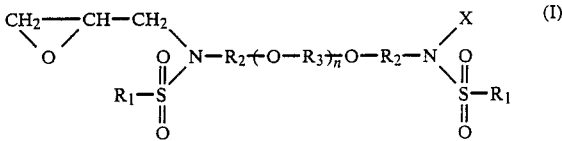

(wherein $R_1$, $R_2$ and $R_3$ each represents an aromatic or aliphatic hydrocarbon group having 1 to 10 carbon atoms, n is an integer of 0 to 30, and X is a hydrogen atom or a glycidyl group).

The present invention also relates to a process for preparing novel glycidyl compounds represented by the general formula (I):

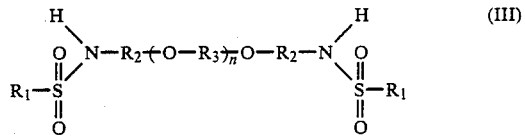

(wherein the symbols are the same as defined above) which comprises reacting ether sulfonamides represented by the following general formula (III):

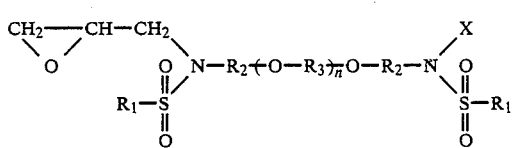

(wherein $R_1$, $R_2$ and $R_3$ each represents an aromatic or aliphatic hydrocarbon group having 1 to 10 carbon atoms, and n is an integer of 0 to 30) with epihalohydrin to prepare their adducts and then reacting the adducts with an aqueous caustic alkali solution.

BRIEF DESCRIPTION OF THE DRAWING

The FIGURE is an infrared absorption spectrum of glycidyl compound 2 obtained in Example 2.

DETAILED DESCRIPTION OF THE INVENTION

Figure 1:
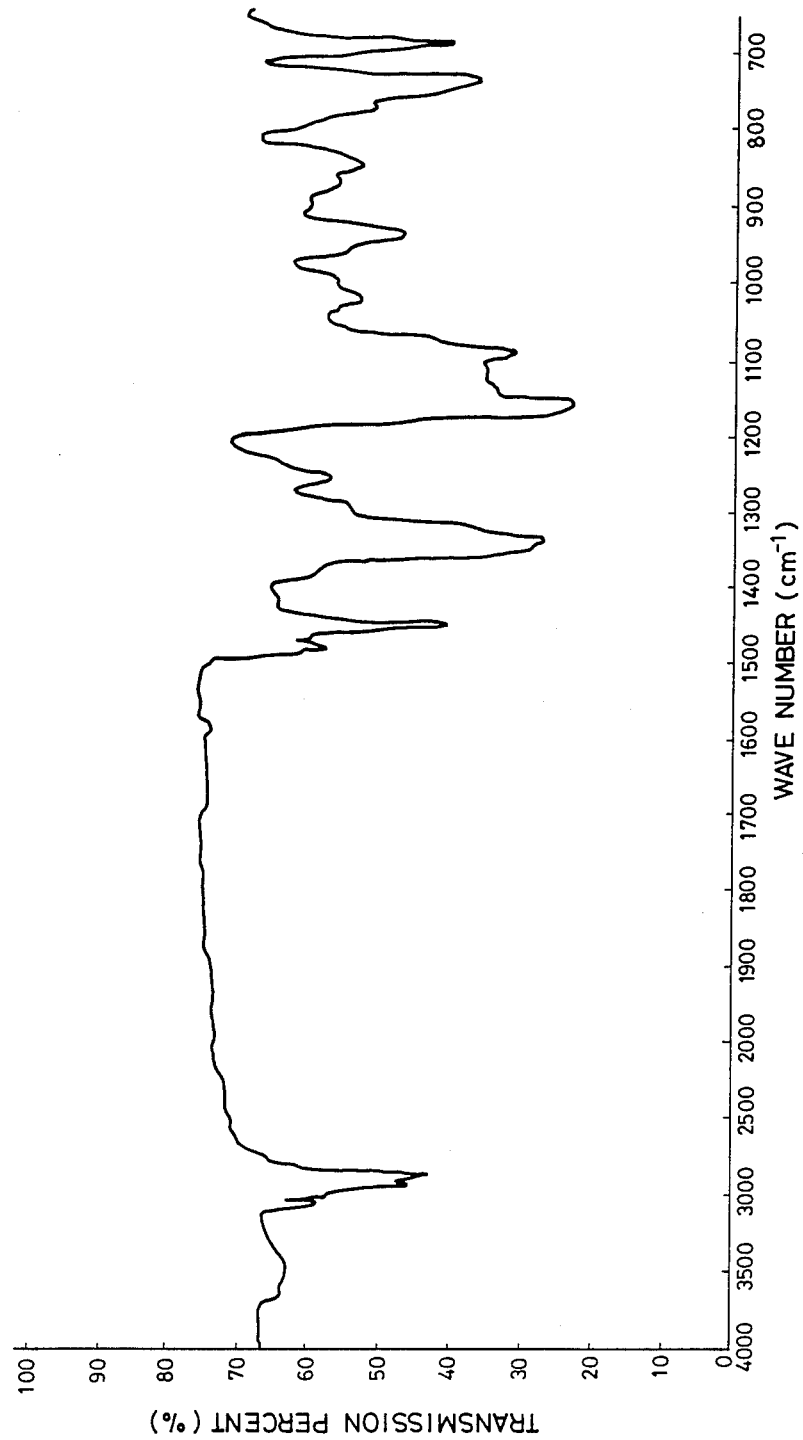

A process for preparation of the glycidyl compounds of the present invention will hereinafter be explained.

Ethersulfonamide compounds represented by the general formula (III) can be easily prepared by reacting ether compounds containing at least two amino groups with aliphatic or aromatic sulfonyl chloride in the presence of a suitable base catalyst. The ether compounds containing at least two amino groups may be aliphatic or aromatic.

Examples are aromatic ether compounds such as 4,4'-diaminodiphenyl ether, 3,4'-diaminodiphenyl ether and bis(aminomethylphenyl) ether, and aliphatic ether compounds such as bis(3-aminopropyl) ether, ethylene glycol bis(3-aminopropyl) ether, diethylene glycol bis(3-aminopropyl) ether and propylene glycol bis(3-aminopropyl) ether. The aliphatic ether compounds include oligomers, i.e., oligoalkylene ether amines which are prepared by cationic polymerization of cyclic ether compounds such as ethylene oxide, propylene oxide and tetrahydrofuran to form oligomers and then aminoalkylating the both ends of the oligomers. As such oligoalkylene ether amines, JEFFAMINE D-230, D-400, D-2000, T-403, etc. produced by Mitsui-Texaco Chemical Co., Ltd. are commercially available. The ether compound can be choosen from the above compounds depending on the object of use of the final glycidyl compound. To obtain glycidyl compounds which are liquid and are of low viscosity, aliphatic compounds are preferred, and furthermore compounds containing a plurality of ether bonds are preferred. If desired, the ether compounds containing the amino group may be used as a mixture comprising two or more thereof.

As sulfonyl chloride, any of aliphatic sulfonyl chlorides such as methanesulfonyl chloride and ethanesulfonyl chloride, and aromatic sulfonyl chlorides such as benzenesulfonyl chloride, o- or p-toluenesulfonyl chloride, 2,4- or 2,5-dimethylbenzenesulfonyl chloride, 1- or 2-naphthalenesulfonyl chloride, and their halides and alkoxy derivatives can be used. Aromatic sulfonyl chlorides are preferred from a viewpoint of ease of synthesis thereof.

The ether sulfonamide compounds of the general formula (III) are prepared from the above amino group containing ether compounds and sulfonyl chlorides by eliminating hydrochloric acid. An excess of amine can be used as the condensing agents. However, from a viewpoint of ease of post-treatment, it is preferred to use a stochiometric amount of an aqueous caustic alkali solution. In the condensation reaction, an inert solvent can be used. Usually the reaction is carried out at a temperature of 10° to 80° C. for a time of 1 to 3 hours, and then the aqueous layer is removed and the inert solvent is distilled off under reduced pressure to obtain the ethersulfonamide compounds.

Glycidylation of the ethersulfonamide compounds thus obtained results in the novel glycidyl compounds of the general formula (I) of the present invention. It has been found that for this glycidylation is particularly suitable a method in which the addition reaction of the ethersulfonamide compound of the general formula (III) and epihalohydrin is carried out in the presence of a Phase Transfer Catalyst and, thereafter, dehydrohalogenation is carried out by the use of an aqueous caustic alkali solution. In accordance with this method, the glycidyl compounds having an epoxy equivalent weight nearly equal to the theoretical value can be obtained in a high yield of more than 90%.

One of the features of the present invention is that in comparison with the glycidyl ether amine known in Japanese Patent Application (OPI) No. 36209/79, the yield can be greatly increased by glycidylating after the conversion of the amine into the sulfonamide.

A process for the preparation of the novel glycidyl compounds of the general formula (I) will hereinafter be explained in more detail.

In the first stage of addition reaction, the ether-sulfonamide compounds of the general formula (III) is reacted with epihalohydrin in the presence of a Phase Transfer Catalyst. The addition reaction is very slow or does not proceed at all if the Phase Transfer Catalyst is not used. The epihalohydrin can be used in any desired amount as long as the molar ratio of the epihalohydrin to the sulfonamide group is not less than 1:1. The epihalohydrin which can be used includes epichlorohydrin, epibromohydrin and epiiodohydrin. The ethersulfonamide compounds of the general formula (III) can be used without purification after the synthesis thereof.

As the Phase Transfer Catalyst, those generally well known, such as quaternary ammonium salts such as tetramethylammonium chloride, tetraethylammonium bromide, and triethylmethylammonium chloride, quaternary phosphonium salts such as triphenylmethylphosphonium chloride and tetraphenylphosphonium chloride, and quaternary arsonium salts can be used. The amount of the Phase Transfer Catalyst used can be chosen appropriately within the range of 0.01 to 100 mol % based on the ethersulfonamide compounds of the general formula (III), with the range of 0.05 to 10 mol % being preferred.

The reaction is carried out at a temperature of 50° to 120° C. for a period of 0.5 to 12 hours and preferably at a temperature of 80° to 110° C. for a period of 1 to 4 hours.

At the second stage, the dehydrohalogenation reaction is carried out using caustic alkali. Caustic alkali which can be used includes sodium hydroxide, potassium hydroxide, calcium hydroxide and magnesium hydroxide. Caustic alkali can be used either as solid or in the form of an aqueous solution. From a viewpoint of ease of handling, an aqueous solution is preferred. The amount of caustic alkali used is 1 to 2 chemical equivalents, preferably 1.1 to 1.5 chemical equivalents per the sulfonamide group. The reaction is carried out at a temperature of 20° to 90° C. for a period of 10 minutes to 3 hours and preferably at a temperature of 40° to 70° C. for a period of 0.5 to 2 hours. As the catalyst for use in the dehydrohalogenation reaction, the Phase Transfer Catalyst used in the addition reaction can be used as it is.

An excessive portion of epihalohydrin may be distilled off prior to the dehydrohalogenation reaction. In this case, as diluents, it is preferred to use inert solvents such as ketones, e.g., methyl ethyl ketone and methyl isobutyl ketone; aromatic hydrocarbons such as benzene, toluene and xylene; and halogenated hydrocarbons such as chloroform and methylene chloride.

After the completion of the reaction, salts formed are removed by filtration or washing with water and unreacted epihalohydrin or the inert solvent used as the diluent are distilled off, whereupon the glycidyl compound of the general formula (I) can be obtained.

The glycidyl compounds thus obtained are transparent or light yellow in color and are in liquid to semi-solid state at room temperature.

The glycidyl compounds of the general formula (I) have a (poly)ether main chain. When the (poly)ether main chain is of the alkylene ether type, the glycidyl compounds of the general formula (I) have a lower viscosity than the usual glycidyl compounds. Furthermore the glycidyl compounds of the general formula (I) provide cured products the modulus of elasticity of which is much lower than those of the usual cured epoxy resins. The glycidyl compounds of the general formula (I) can be cured alone or in combination with other epoxy compounds. Curing agents which are commonly used in the usual epoxy resins can be used. Examples are acid anhydrides, aromatic or aliphatic amines, heterocyclic amines, and organic acids such as polyphenols. If suitable curing agents are chosen, there can be obtained cured products which are excellent in flexibility and elongation.

The glycidyl compounds of the present invention are excellent in compatibility and thus can be mixed with the other glycidyl compounds in any desired ratio. The amount of the other epoxy compound compounded is chosen within the range of 0.01 to 100 parts by weight per part by weight of the glycidyl compound of the present invention. In particular, by mixing the glycidyl compounds of the present invention with epoxy compounds having a high cross-linking density, suitable elongation can be imparted to the cured products. Epoxy resins which can be used in admixture with the glycidyl compounds of the present invention include polyglycidyl esters exemplified by the epi-bis type compound, polyglycidyl esters effected by glycidylating a phthalic acid, cyclohexane dicarboxylic acid and the like; glycidyl amines effected by glycidylating an aniline a methylenediamine and the like; glycidyl compounds effected by glycidylating an aminophenols; polyglycidyl ethers effected by glycidylating a phenol novolak, a cresol novolak and the like; and an alicyclic polyepoxy compounds.

To the glycidyl compounds of the present invention can be added, as well as the curing agent, if desired, various additives such as a curing accelerating agent such as tertiary amines and imidazoles; a filler such as silica and talc; a reinforcement such as glass fibers and carbon fibers; pigments and flame retardants.

The glycidyl compounds of the present invention are useful as molding materials, paints, adhesives, sealing materials, laminating materials and matrix resins of FRP. Other epoxy compounds can be improved in flexibility, elongation, adhesive properties and impact resistance by mixing with the glycidyl compounds of the present invention.

The present invention is described in greater detail with reference to the following examples although it is not intended to be limited thereto. Unless otherwise indicated, all parts, percents, and ratios are by weight.

PREPARATION EXAMPLE 1

Preparation of Ethersulfonamide Compound

In a 200-milliliter four-necked flask were charged 11.02 g (50 millimoles) of diethylene glycol bis(3-aminopropyl) ether, 20 ml of chloroform and 20 ml (100 millimoles) of a 5N aqueous solution of sodium hydroxide, and then 17.66 g (100 millimoles) of benzenesulfonyl chloride was dropped over a time of 10 minutes while cooling with cold water from the outside. The contents were then heated to 45° C. and stirred for one hour. An organic layer was separated by decantation, and chloroform was distilled off to obtain 24.91 g (99.5% of the theoretical yield) of 4,7,10-trioxatridecane-1,13-bisbenzenesulfonamide.

PREPARATION EXAMPLE 2

Preparation of Ethersulfonamide Compound

The procedure of Preparation Example 1 was repeated except that 8.81 g (50 millimoles) of ethylene glycol bis(3-aminopropyl) ether was used in place of diethyleneglycol bis(3-aminopropyl) ether, to thereby obtain 25.62 g (90.1% of the theoretical yield) of 4,7-dioxadecane-1,10-bisbenzenesulfonamide.

PREPARATION EXAMPLE 3

Preparation of Ethersulfonamide Compound

The procedure of Preparation Example 1 was repeated except that 12.50 g of JEFFAMINE D-230 having 125 g/eq. of amine equivalent was used in place of 11.02 g of ethylene glycol bis(3-aminopropyl)ether to thereby obtain 26.06 g of sulfonamide compound. The sulfonamide compound thus obtained is hereinafter called "Sulfonamide Compound 3".

PREPARATION EXAMPLE 4

Preparation of Ethersulfonamide Compound

The procedure of Preparation Example 1 was repeated except that 21.83 g of JEFFAMINE D-400 having 218 g/eq. of amine equivalent was used in place of 11.02 g of ethylene glycol bis(3-aminopropyl)ether to thereby obtain 35.78 g of sulfonamide compound. The sulfonamide compound thus obtained is hereinafter called "Sulfonamide Compound 4".

PREPARATION EXAMPLE 5

Preparation of Ethersulfonamide Compound

The procedure of Preparation Example 1 was repeated except that 104.17 g of JEFFAMINE D-2000 having 1042 g/eq. of amine equivalent was used in place of 11.02 g of ethylene glycol bis(3-aminopropyl)ether to thereby obtain 127.50 g of sulfonamide compound. The sulfonamide compound thus obtained is hereinafter called "Sulfonamide Compound 5".

PREPARATION EXAMPLE 6

Preparation of Ethersulfonamide Compound

The procedure of Preparation Example 1 was repeated except that 15.50 g of JEFFAMINE T-403 having 155 g/eq. of amine equivalent was used in place of 11.02 g of ethylene glycol bis(3-aminopropyl)ether to thereby obtain 29.65 g of sulfonamide compound. The sulfonamide compound thus obtained is hereinafter called "Sulfonamide Compound 6".

PREPARATION EXAMPLE 7

Preparation of Ethersulfonamide Compound

Santamine TM-100 comprising oligotetramethyleneglycol in main chain produced by Sanyo Kasei Kogyo K.K. was adopted as an oligoalkylene etheramine. An amine equivalent of Santamine TM-100 was 591 g/eq.

The procedure of Preparation Example 1 was repeated except that 59.10 g of TM-100 was used in place of 11.02 g of ethylene glycol bis(3-aminopropyl)ether thereby obtaining 73.02 g of sulfonamide compound. The sulfonamide compound thus obtained is hereinafter called "Sulfonamide compound 6".

EXAMPLE 1

25.31 g (100 millimoles) of 4,7,10-trioxatridecane-1,13-bisbenzenesulfonamide, 46.3 g (500 millimoles) of epichlorohydrin and 0.455 g (2 millimoles) of benzyltriethylammonium chloride were charged in a 200-milliliter four-necked flask and reacted at 95°-100° C. A decrease in the N-H absorption was traced by the infrared absorption spectrum, and the reaction was completed in 3 hours. The contents were cooled to 50° C. and 24 ml (120 millimoles) of a 5N aqueous solution of sodium hydroxide was dropped thereto over 10 minutes while vigorously stirring. After the completion of the addition, stirring was continued for 1.5 hours. An aqueous layer containing salts was separated by decantation, and the organic layer was washed four times with each 100 ml of deionized water. Excessive epichlorohydrin was distilled off under reduced pressure to obtain 29.77 g (97.2% of the theoretical yield) of 4,7,10-trioxatridecane-1,13-bis(N-glycidylbenzenesulfonamide). The epoxy equivalent weight as determined by the hydrochloric acid-pyridine method was 324 g/eq. (theoretical value: 306 g/eq). The glycidyl compound thus obtained is hereinafter called "Glycidyl Compound 1".

EXAMPLE 2

The procedure of Example 1 was repeated except that 22.82 g (100 millimoles) of 4,7-dioxadecane-1,10-bisbenzenesulfonamide as obtained in Preparation Example 2 was used in place of 4,7,10-trioxatridecane-1,13-bisbenzenesulfonamide, to thereby obtain 25.62 g (90.1% of the theoretical yield) of 4,7-dioxadecane-1,10-bis(N-glycidylbenzenesulfonamide). The epoxy equivalent weight was 307 g/eq. (theoretical value: 284 g/eq). The glycidyl compound thus obtained is hereinafter called "Glycidyl Compound 2".

EXAMPLE 3

The procedure of Example 1 was repeated except that 26.06 g of Sulfonamide compound 3 obtained in the Preparation Example 3 was used in place of 25.31 g of 4,7,10-trioxatridecane-1,13-bisbenzenesulfonamide, to thereby obtain 31.95 g of glycidyl compound having 344 g/eq. of epoxy equivalent weight. The glycidyl compound thus obtained is hereinafter called "Glycidyl Compound 3".

EXAMPLE 4

The procedure of Example 1 was repeated except that 35.78 g of Sulfonamide Compound 4 obtained in the Preparation Example 4 was used in place of 25.31 g of 4,7,10-trioxatridecane-1,13-bisbenzenesulfonamide to thereby obtain 42.50 g of glycidyl compound having 432 g/eq. of epoxy equivalent weight. The glycidyl compound thus obtained is hereinafter called "Glycidyl Compound 4".

EXAMPLE 5

The procedure of Example 1 was repeated except that 127.50 g of Sulfonamide Compound 5 obtained in the Preparation Example 5 was used in place of 25.31 g of 4,7,10-trioxatridecane-1,13-bisbenzenesulfonamide to thereby obtain 98.33 g of glycidyl compound having 2553 g/eq. of epoxy equivalent weight. The glycidyl compound thus obtained is hereinafter called "Glycidyl Compound 5".

EXAMPLE 6

The procedure of Example 1 was repeated except that 29.65 g of Sulfonamide Compound 6 obtained in Preparation Example 6 was used in place of 25.31 g of 4,7,10-trioxatridecane-1,13-bisbenzenesulfonamide to thereby obtain 26.20 g of glycidyl compound having 435 g/eq. of epoxy equivalent weight. The glycidyl compound thus obtained is hereinafter called "Glycidyl Compound 6".

EXAMPLE 7

The procedure of Example 1 was repeated except that 73.02 g of Sulfonamide Compound 7 obtained in the Preparation Example 7 was used in place of 25.31 g of 4,7,10-trioxatridecane-1,13-bisbenzenesulfonamide to thereby obtain 86.37 g of glycidyl compound having 957 g/eq. of epoxy equivalent weight. The glycidyl compound thus obtained is hereinafter called "Glycidyl Compound 7".

APPLICATION EXAMPLES 1 TO 5

Using the glycidyl compounds obtained in Examples 1 and 2, cured products were obtained. Compounding ratios, curing conditions, and physical properties of the cured products are shown in Table 1. Parts in the table are by weight. The physical properties were measured according to Testing Methods for Thermosetting Plastics JIS K-6911.

COMPARATIVE APPLICATION EXAMPLE 1

Using tetraglycidyldiaminodiphenylmethane, (epoxy equivalent weight: 120 g/eq.), cured products were obtained in the same manner as in Application Examples 1 to 5. The results are shown in Table 1.

APPLICATION EXAMPLE 5

The glycidyl compound obtained in Example 2 was stored at room temperature for 3 months. The epoxy equivalent weight was again measured and found to be 313 g/eq. Thus the storage stability was good.

TABLE 1

|  | Application Example | | | | | Comparative Application Example 1 |
|---|---|---|---|---|---|---|
|  | 1 | 2 | 3 | 4 | 5 |  |
| Glycidyl Compound 1 (Parts) | 100 | 50 | 50 | — | — | — |
| Glycidyl Compound 2 (Parts) | — | — | — | 100 | 50 | — |
| TGDDM[1] (Parts) | — | — | 50 | — | 50 | 100 |
| Ep828[2] (Parts) | — | 50 | — | — | — | — |
| NMA[3] (Parts) | 44.9 | 62.5 | 86.0 | 49.3 | 85.6 | 122 |
| BDMA[4] (Parts) | 2.0 | 2.0 | 2.0 | 2.0 | 2.0 | 2.0 |
| Curing Condition | 100° C./1 Hr + 150° C./2 Hr + 180° C./5 Hr | | | | | |
| Flexural Strength (kg/mm$^2$) | 12.9 | 5.4 | 8.9 | 6.2 | 8.5 | 3.4 |
| Modulus of Bending Elasticity (kg/mm$^2$) | 297.5 | 315.9 | 256.9 | 342.8 | 365.3 | 361.8 |
| Bending Elongation (%) | 6.7 | 1.9 | 3.7 | 1.7 | 2.2 | 1.1 |
| HDT (°C.) | 60.8 | 94.6 | 143.8 | 68.4 | 122.8 | 211.7 |

Remarks:
1 Tetraglycidyldiaminodiphenylmethane (epoxy equivalent weight 120 g/eq).
2 Epicoat 828 (Yuka Shell Epoxy Co., Ltd.) (epoxy equivalent weight 189 g/eq).
3 Anhydrous methylnadic acid (Hitachi Kasei Co., Ltd.)
4 Benzyldimethylamine While the invention has been described in detail and with reference to specific embodiment thereof, it will be apparent to one skilled in the art that various changes and modifications can be made therein without departing from the spirit and scope thereof.

What is claimed is:

1. A glycidyl compound containing at least one ether bond in the main chain thereof represented by general formula (I):

$$CH_2\text{---}CH\text{---}CH_2\text{---}N(SO_2R_1)\text{---}R_2\text{---}(O\text{---}R_3)_n\text{---}O\text{---}R_2\text{---}N(SO_2R_1)\text{---}X \quad (I)$$

(wherein $R_1$, $R_2$ and $R_3$ each represents an aromatic or aliphatic hydrocarbon group having 1 to 10 carbon atoms, n is an integer of 0 to 30, and X is a hydrogen atom or a glycidyl group).

2. The compound as claimed in claim 1 wherein $R_2$ is $-(CH_2)_{\overline{m}}$ and $R_3$ is $-C_2H_4$ (wherein m is an integer of 1 to 10).

3. The compound as claimed in claim 1, wherein $R_2$ is $-(CH_2)_{\overline{m}}$ and

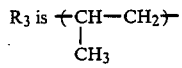

(wherein m is an integer of 1 to 10).

4. The compound as claimed in claim 1, wherein $R_2$ is $-(CH_2)_{\overline{m}}$ and $R_3$ is $-(CH_2)_{\overline{4}}$ (wherein m is an integer of 1 to 10).

5. The compound as claimed in claim 1, wherein $R_2$ is $-(CH_2)_{\overline{3}}$.

6. The compound as claimed in claim 2 $R_2$ is $-(CH_2)_{\overline{3}}$.

7. The compound as claimed in claim 3 $R_2$ is $-(CH_2)_{\overline{3}}$.

8. The compound as claimed in claim 4 $R_2$ is $-(CH_2)_{\overline{3}}$.

9. The compound as claimed in claim 1, wherein $R_1$ is an aromatic hydrocarbon group having from 6 to 10 carbon atoms.

10. The compound as claimed in claim 2, wherein $R_1$ is an aromatic hydrocarbon group having from 6 to 10 carbon atoms.

11. The compound as claimed in claim 3, wherein $R_1$ is an aromatic hydrocarbon group having from 6 to 10 carbon atoms.

12. The compound as claimed in claim 4, wherein $R_1$ is an aromatic hydrocarbon group having from 6 to 10 carbon atoms.

13. The compound as claimed in claim 5, wherein $R_5$ is an aromatic hydrocarbon group having from 6 to 10 carbon atoms.

* * * * *